United States Patent
He et al.

(10) Patent No.: US 9,370,296 B2
(45) Date of Patent: Jun. 21, 2016

(54) MEDICAL DIAGNOSTIC SYSTEM

(75) Inventors: Lai He, Shanghai (CN); Yun Zou, Baulkham Hills (AU); James J. Shortt, Trim (IE); Stephen A. Montgomery, Virginia (IE); Michael McAtamney, Navan (IE)

(73) Assignee: Welch Allyn, Inc., Skaneateles Falls, NY (US)

( * ) Notice: Subject to any disclaimer, the term of this patent is extended or adjusted under 35 U.S.C. 154(b) by 1178 days.

(21) Appl. No.: 13/308,480

(22) Filed: Nov. 30, 2011

(65) Prior Publication Data

US 2013/0137939 A1    May 30, 2013

(51) Int. Cl.
| | | |
|---|---|---|
| A61B 5/00 | (2006.01) | |
| A61B 1/00 | (2006.01) | |
| A61B 1/227 | (2006.01) | |
| A61B 3/12 | (2006.01) | |
| A61B 5/022 | (2006.01) | |

(52) U.S. Cl.
CPC .............. *A61B 1/00131* (2013.01); *A61B 1/227* (2013.01); *A61B 3/12* (2013.01); *A61B 5/022* (2013.01); *A61B 2560/0406* (2013.01); *A61B 2560/0431* (2013.01)

(58) Field of Classification Search
None
See application file for complete search history.

(56) References Cited

U.S. PATENT DOCUMENTS

| | | |
|---|---|---|
| 5,376,070 A | 12/1994 | Purvis et al. |
| 5,871,465 A | 2/1999 | Vasko |
| D434,142 S | 11/2000 | Cheney et al. |
| D446,854 S | 8/2001 | Cheney, II et al. |
| D452,564 S | 12/2001 | Micinski et al. |
| 6,435,109 B1 | 8/2002 | Dell et al. |
| D504,726 S | 5/2005 | Ryan |
| D511,008 S | 10/2005 | Ryan |
| D516,026 S | 2/2006 | Barrett et al. |
| D547,863 S | 7/2007 | Heinsch |
| D554,759 S | 11/2007 | Barker |
| D569,981 S | 5/2008 | Collins |
| D577,118 S | 9/2008 | Yodfat et al. |
| D601,258 S | 9/2009 | Bell et al. |
| D601,259 S | 9/2009 | Guthrie et al. |
| D604,418 S | 11/2009 | Jones et al. |
| D617,911 S | 6/2010 | Freeman et al. |
| D625,014 S | 10/2010 | Hansen et al. |
| D625,015 S | 10/2010 | Hansen et al. |
| 7,843,167 B2 * | 11/2010 | DeRome et al. .............. 320/112 |
| D642,279 S | 7/2011 | Barker et al. |

(Continued)

OTHER PUBLICATIONS

ADC Complete 2.5v Instrument Set, copyright 2010 Redding Medical™ Equipment, 2 pages.

(Continued)

*Primary Examiner* — Brian T Gedeon
(74) *Attorney, Agent, or Firm* — Merchant & Gould P.C.

(57) ABSTRACT

An integrated portable medical diagnostic system (PMDS) provides easy and convenient access to one or more medical instruments for healthcare practitioners. The PMDS is utilized in an outpatient workflow in which the practitioner generally remains stationary, while patients rotate to and from the practitioner over the course of a medical examination or procedure. The PMDS includes a body including a plurality of compartments, a first compartment defines a first receptacle for a blood pressure monitor, a second compartment adjacent the first compartment defines a second receptacle for an otoscope and an ophthalmoscope, and a third compartment adjacent the second compartment defines a third receptacle for a thermometer.

3 Claims, 11 Drawing Sheets

(56) References Cited

U.S. PATENT DOCUMENTS

| | | |
|---|---|---|
| D642,691 S | 8/2011 | Barker et al. |
| 8,214,566 B2 * | 7/2012 | Edwards et al. ............... 710/63 |
| D697,625 S | 1/2014 | Montgomery et al. |
| 2008/0281167 A1 | 11/2008 | Soderberg et al. |
| 2011/0022748 A1 | 1/2011 | Edwards et al. |

OTHER PUBLICATIONS

Basic Medical Student Package #1, copyright 2010 Redding Medical™ Equipment, 2 pages.

Keeler Practitioner Otoscope and Ophthalmoscope Desk Set, copyright 2011 Williams Medical Supplies, Ltd., 1 page.

Medical Student Clinical Medical Equipment Starter Kit, copyright 2005-2011, 3 pages.

Riester Ri-Mini Otoscope & Ophthalmoscope Combination Kit, copyright 1995-2011 Steele Supply Company, 1 page.

Design U.S. Appl. No. 29/207,593, filed Nov. 30, 2011.

Welch Allyn Extended Care Catalog, copyright 2011 Welch Allyn, 10 pages.

* cited by examiner

MEDICAL DIAGNOSTIC SYSTEM

BACKGROUND

Healthcare practitioners, such as nurses and physicians, use various types of therapeutic and diagnostic tools to assist with the task of providing healthcare to a patient. In a typical outpatient setting, a patient enters a private examination room and waits for a particular practitioner to arrive to begin an examination. The practitioner may have other patients in different private examination rooms also waiting for an examination. This workflow may be considered "patient-centric" because the patient generally remains stationary, while the practitioner rotates between other patients. However, such a workflow is not the only manner by which a practitioner can provide healthcare in an outpatient setting.

SUMMARY

In one aspect, a medical diagnostic apparatus is disclosed. The apparatus includes a body including a plurality of compartments, a first compartment defines a first receptacle for a blood pressure monitor, a second compartment adjacent the first compartment defines a second receptacle for an otoscope and an ophthalmoscope, and a third compartment adjacent the second compartment defines a third receptacle for a thermometer.

In another aspect, an integrated portable medical diagnostic system including a blood pressure monitor, an otoscope, an ophthalmoscope, a thermometer, and an apparatus is disclosed. The apparatus including a body defining a plurality of compartments, a first compartment defines a first receptacle for the blood pressure monitor, a second compartment adjacent the first compartment defines a second receptacle for the otoscope and the ophthalmoscope, and a third compartment adjacent the second compartment defines a third receptacle for the thermometer; and at least one power supply arranged within the body.

In yet another aspect, a method for using a medical diagnostic apparatus to perform an examination on a patient is disclosed. The method includes: (i) retrieving at least one tool selected from the group comprising: a blood pressure monitor; an otoscope; an ophthalmoscope; and a thermometer, the tool being stored in a medical diagnostic apparatus, the apparatus including: a body formed of a thermoplastic elastomer and defining a plurality of compartments, wherein a first compartment defines a first receptacle for the blood pressure monitor, a second compartment adjacent the first compartment defines a second receptacle for the otoscope and the ophthalmoscope, and a third compartment adjacent the second compartment defines a third receptacle for the thermometer; a bracket coupled to a portion of the first compartment, the bracket configured to support an aneroid of the blood pressure monitor; and a first and second power supply arranged within the body, wherein the second receptacle comprises: a pocket arranged as storage for disposable and reusable tips of the otoscope and ophthalmoscope; and a plurality of ports each coupled to the first power supply and configured to supply power to the otoscope and ophthalmoscope, wherein each of the plurality of ports are arranged to support either one of the otoscope and ophthalmoscope in an approximately vertical orientation, and the third receptacle comprises a cradle arranged to support the thermometer in an approximately horizontal orientation, the cradle comprising contacts coupled to the second power supply and configured to supply power to the thermometer; (ii) performing at least one diagnostic medical procedure on the patient utilizing the at least diagnostic tool retrieved in step (i); (iii) recording results of the at least one diagnostic medical procedure into at least one of an electronic medical record and a paper record associated with the patient; (iv) dismissing the patient from the examination; and (v) at least intermittently repeating steps (i)-(iv).

This Summary is provided to introduce a selection of concepts, in a simplified form, that are further described below in the Detailed Description. This Summary is not intended to be used in any way to limit the scope of the claimed subject matter. Rather, the claimed subject matter is defined by the language set forth in the Claims of the present disclosure.

DETAILED DESCRIPTION

The present disclosure is directed to an integrated portable medical diagnostic system (PMDS) that provides easy and convenient access to one or more medical instruments for healthcare practitioners. In one embodiment, a PMDS is utilized in a "practitioner-centric" outpatient workflow in which the practitioner generally remains stationary, while patients rotate to and from the practitioner over the course of a medical examination or procedure.

Figure 1:
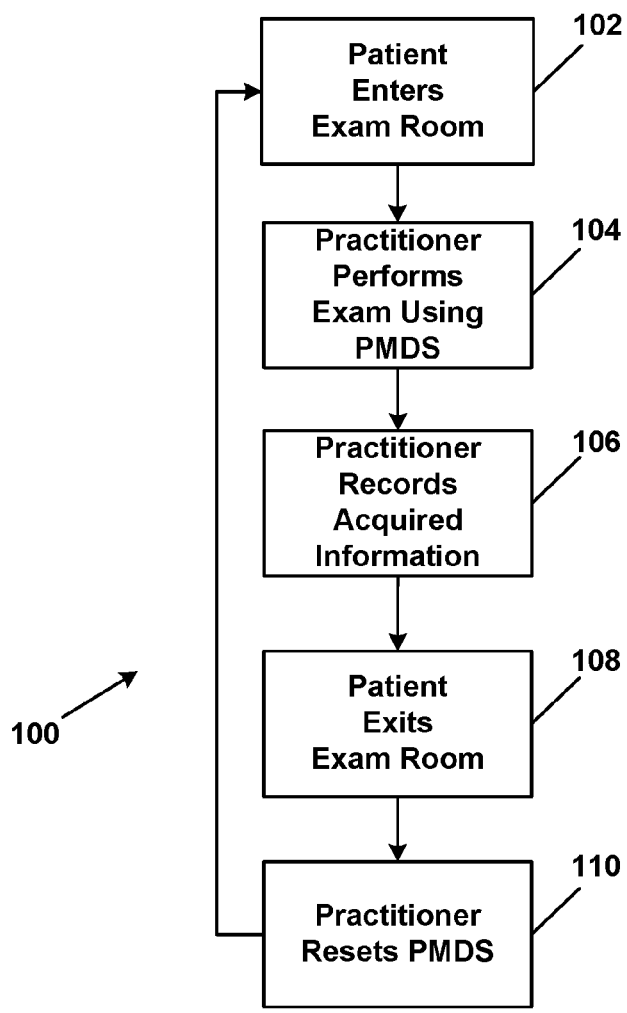
FIG. 1 shows an example workflow incorporating a portable medical diagnostic system (PMDS) according to the principles of the present disclosure.

For example, referring now to FIG. 1, an example workflow 100 is shown according to the principles of the present disclosure.

The workflow 100 beings at a step 102, in which a patient enters an examination room for the purpose of undergoing an examination or one or more minor or intermediate diagnostic medical procedures. An example of a diagnostic medical procedure includes an eye exam, an ear exam, blood pressure measurement, and temperature measurement. Other embodiments are possible. For example, the patient may enter the examination room for the purpose of undergoing at least one therapeutic medical procedure exclusive of, or in addition to, a diagnostic medical procedure(s). Still other embodiments are possible.

Once the patient enters the examination room, the patient is directed to a station within the room that includes one or more furnishings and at least one PMDS. An example station includes a desk with chairs, with a PMDS positioned to a top surface of the desk. Other embodiments are possible. For example, a PMDS can generally be positioned to any type of stand surface within the examination room such as, for example, a counter surface, a table surface, a shelf surface, and any other type of furnishing surface as desired.

Next, at a step 104, the practitioner performs an examination on the patient using one or more of a plurality of tools or instruments stored to the PMDS. For example, the practitioner may retrieve an ophthalmoscope from the PMDS in the event of an eye exam, an otoscope in the event of an ear exam, a blood pressure monitor in the event of a blood pressure monitoring procedure, and a thermometer in the event of a temperature monitoring procedure. Other embodiments are possible. For example, the PMDS can generally be configured to include any number of instruments designed to obtain a diagnostic reading or implement a therapy as desired.

Next, at a step 106, the practitioner records any relevant patient information acquired during the examination. For example, the practitioner may enter diagnostic measurement information and/or other patient specific information into an electronic medical record (EMR) and/or a paper record associated with the patient. Other embodiments are possible. For example, in some embodiments, patient information acquired during the examination is recorded within an EMR via a wireless and/or hardwired communication connection between a given instrument and a computing device. Still other embodiments are possible.

Next, at a step 108, the patient exits the examination room, and, at a step 110, the practitioner resets or prepares the PMDS for a subsequent patient. In some embodiments, this includes sanitizing all or a portion of the PMDS, and one or more of the instruments stored to the PMDS that were used during the examination. Other embodiments are possible.

Workflow then returns to step 102 in which a different patient enters the examination room. In this manner, the PMDS is utilized in a "practitioner-centric" workflow periodically or at least intermittently in which the practitioner generally remains stationary, while patients rotate to and from the practitioner over the course of a medical examination or procedure. Additionally, in the example of a station having a desk with chairs, the practitioner may remain seated within a chair during the examination. In this example, and with a PMDS positioned to a top surface of the desk, the practitioner has easy and convenient access to the instruments stored to the PMDS.

FIGS. 2-11 show an example PMDS 200 in accordance with the present disclosure. In one embodiment, the PMDS 200 is utilized in the "practitioner-centric" workflow 100 described above in connection with FIG. 1. Other embodiments are possible. For example, the PMDS 200 may generally be utilized in any situation in which it is desirable to have easy and convenient access to one or more medical instruments for healthcare practitioners.

Figure 2:
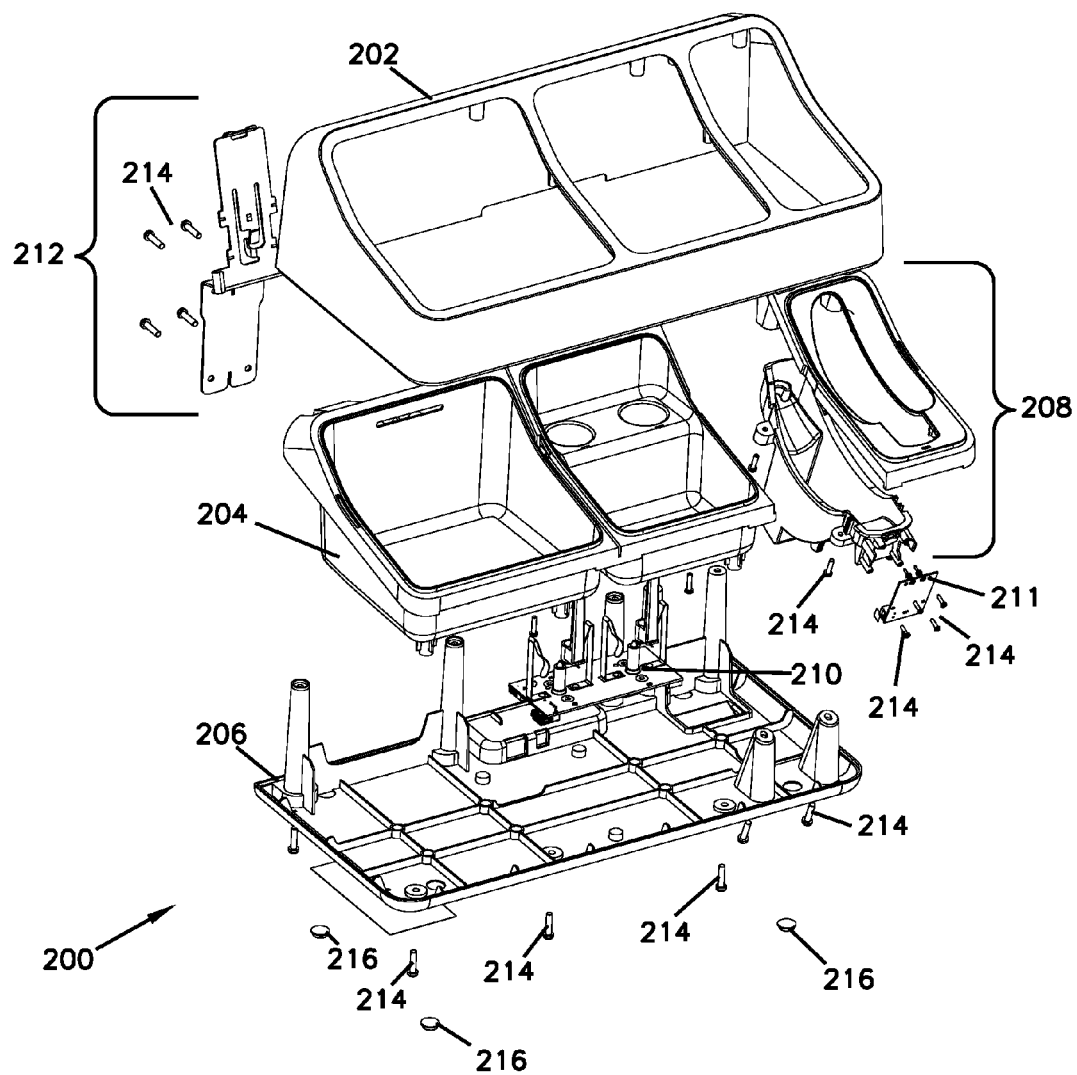
FIG. 2 shows an exploded first perspective view of an example PMDS excluding medical instruments.

Referring now to FIG. 2, an exploded perspective view of the PMDS 200 is shown excluding a plurality of medical instruments. The PMDS 200 includes a first section 202, a second section 204, a third section 206, a fourth section 208, a first power supply 210, a second power supply 211, and a bracket 212. A plurality of fasteners 214, such as screws or rivets, are utilized to secure respective components of the PMDS 200 to one another. Additionally, a plurality of supports 216, when securely positioned to the third section 206, are utilized to prevent unintentional shifting of PMDS 200 when the PMDS 200 is positioned to a surface, such as a desktop.

In one embodiment, one or more of the respective components of the PMDS 200 as shown in FIG. 2 are formed of a thermoplastic elastomer. However, other embodiments are possible. For example, in some embodiments, the bracket 212 and/or fasteners 214 are formed of a metallic material, and the supports 216 are formed of a rubberized material. Still other embodiments are possible.

Figure 8:
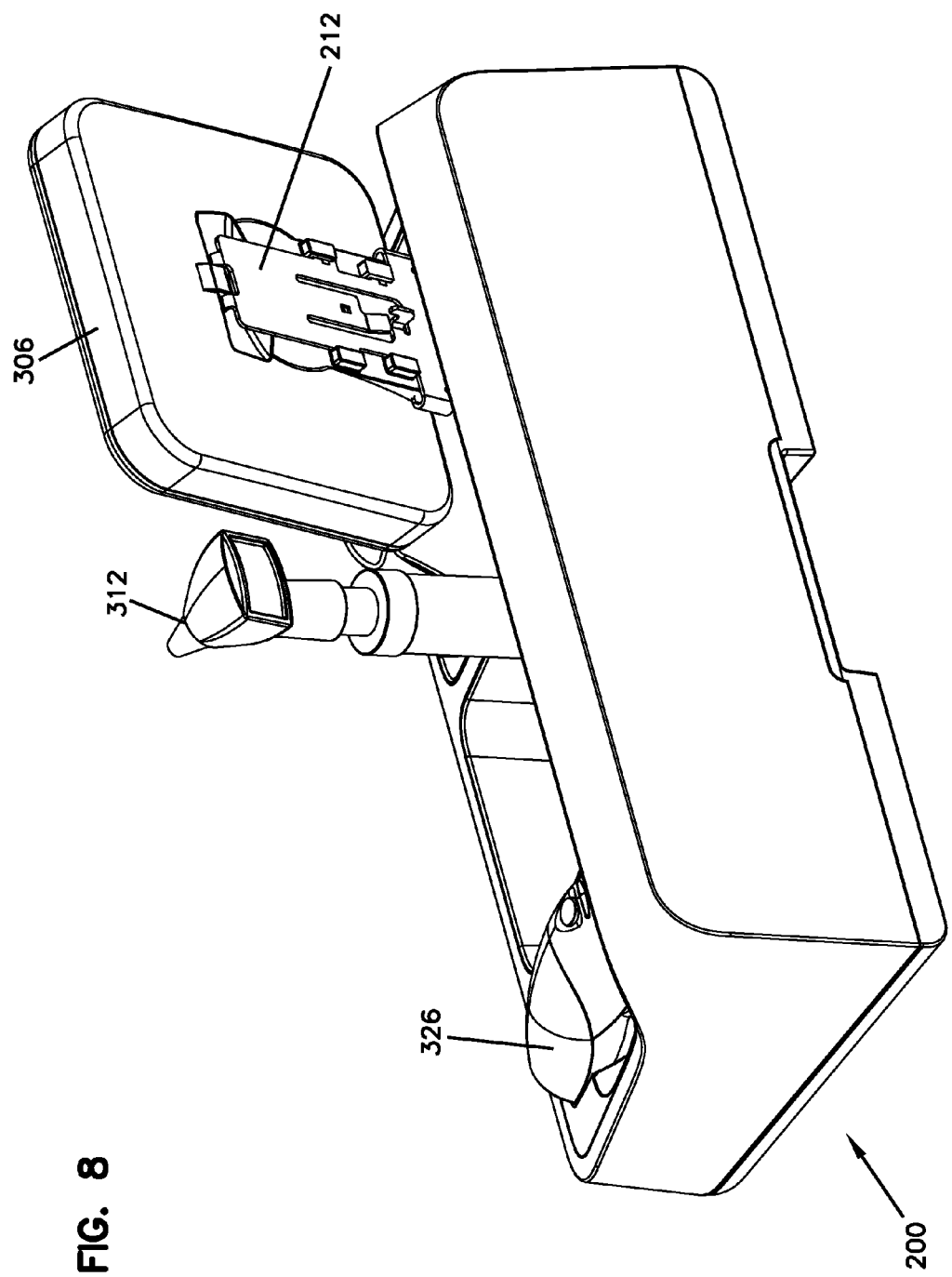
FIG. 8 shows a second perspective view of the PMDS of FIG. 4.
Figure 9:
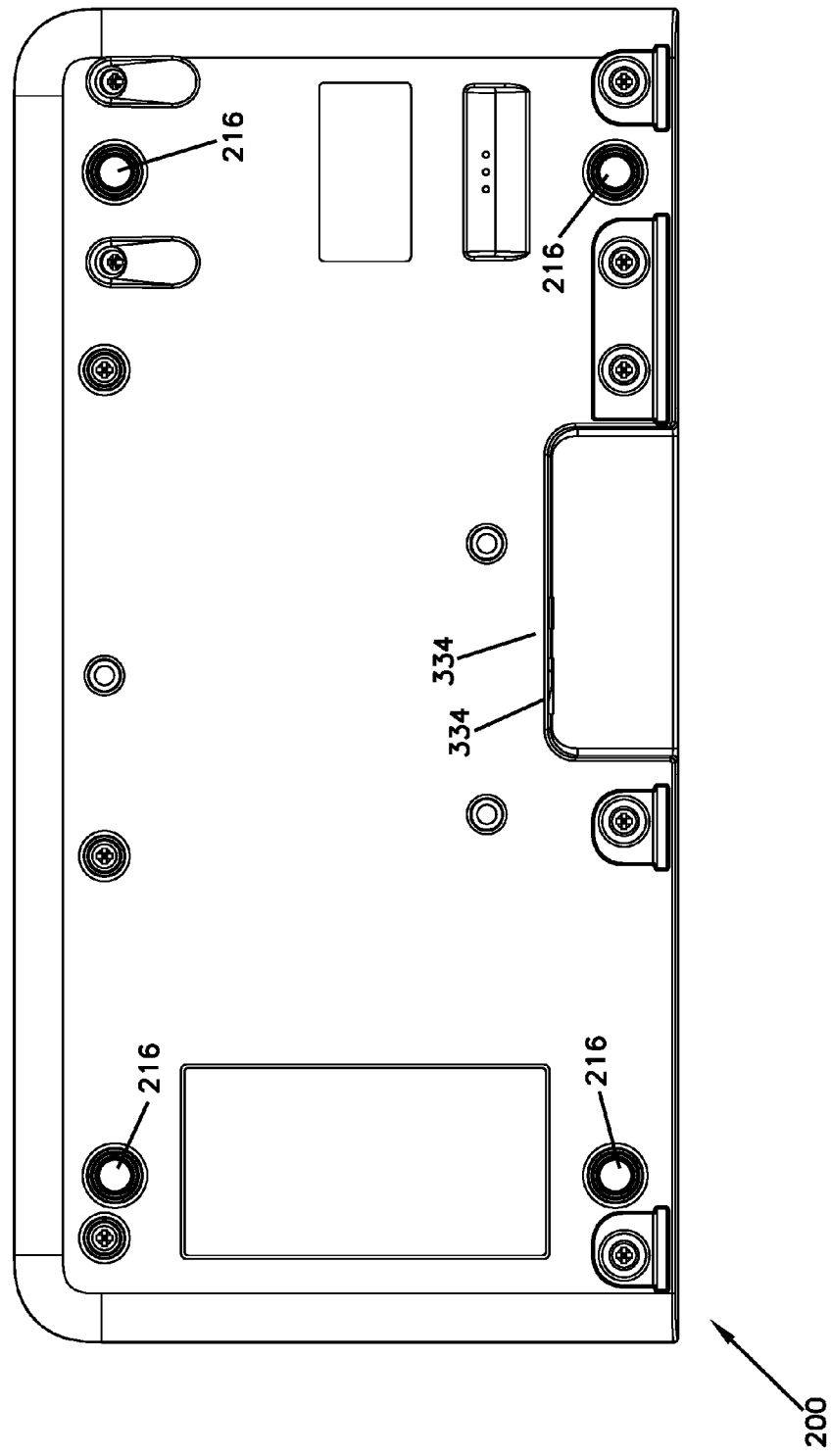
FIG. 9 shows a bottom view of the PMDS of FIG. 4.
Figure 10:
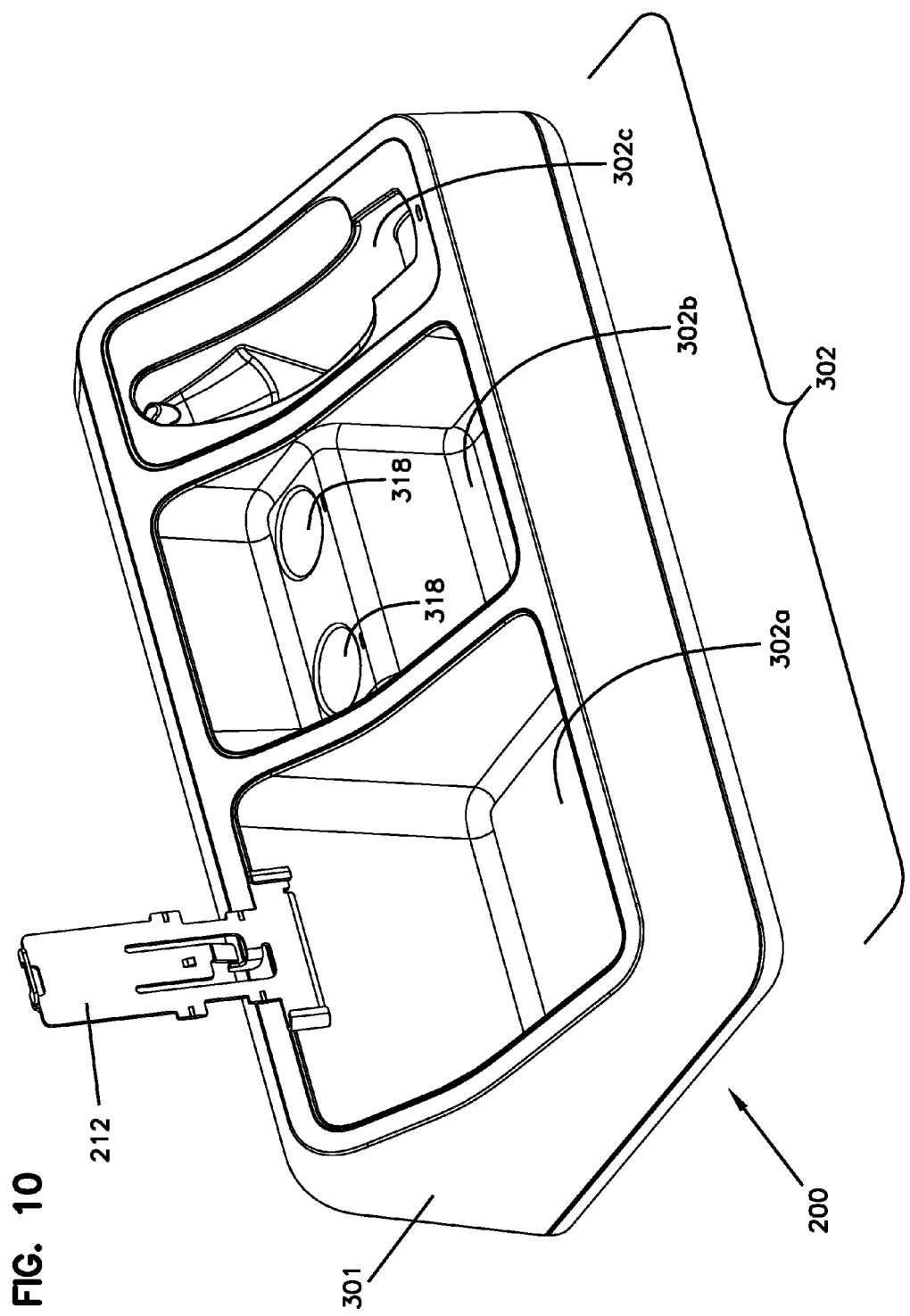
FIG. 10 shows the PMDS of FIG. 2 excluding medical instruments.
Figure 11:
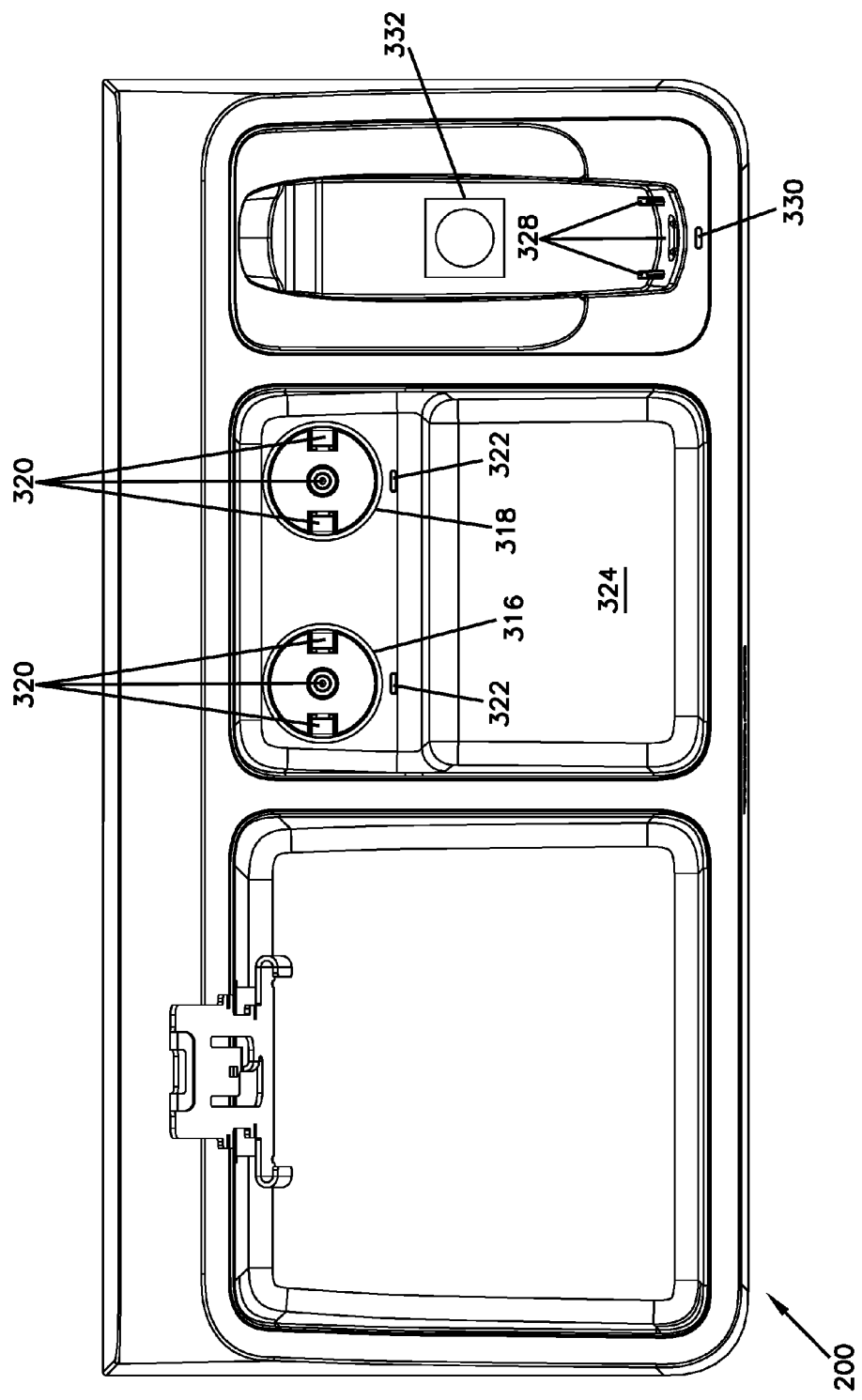
FIG. 11 shows the PMDS of FIG. 6 excluding medical instruments.

Referring now to FIGS. 3-11, the example PMDS 200 is shown in an assembled configuration. FIGS. 3-9 show the PMDS 200 including a plurality of medical instruments positioned either in proximity thereto or stored thereto, and FIGS. 10-11 show the PMDS 200 excluding the medical instruments, discussed in further detail below.

In general, the PMDS 200, when assembled, comprises a body 301. In one embodiment, the body 301 is about 18 inches in length, about 8 inches in width, and about 4 inches in height, or equivalently, about 46 centimeters in length, about 20 centimeters in width, and about 10 centimeters in height. Other embodiments are possible.

The body 301 includes plurality of compartments 302 (see e.g., FIG. 3, FIG. 10) each arranged as a receptacle for one or more medical tools or instruments a healthcare practitioner might typically use in an outpatient setting or workflow.

Figure 3:
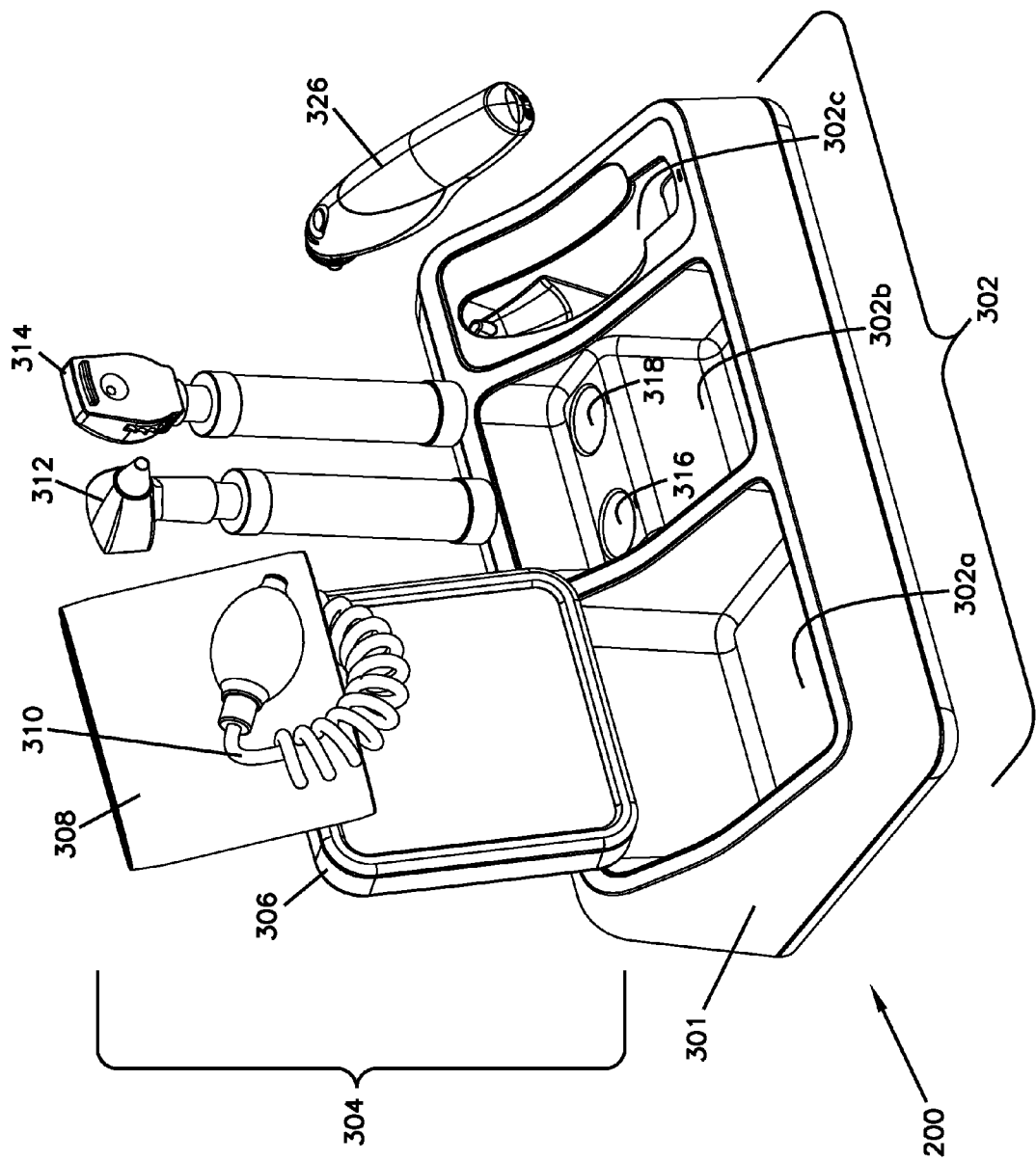
FIG. 3 shows the PMDS of FIG. 2 in an assembled arrangement including medical instruments positioned in proximity thereto.
Figure 4:
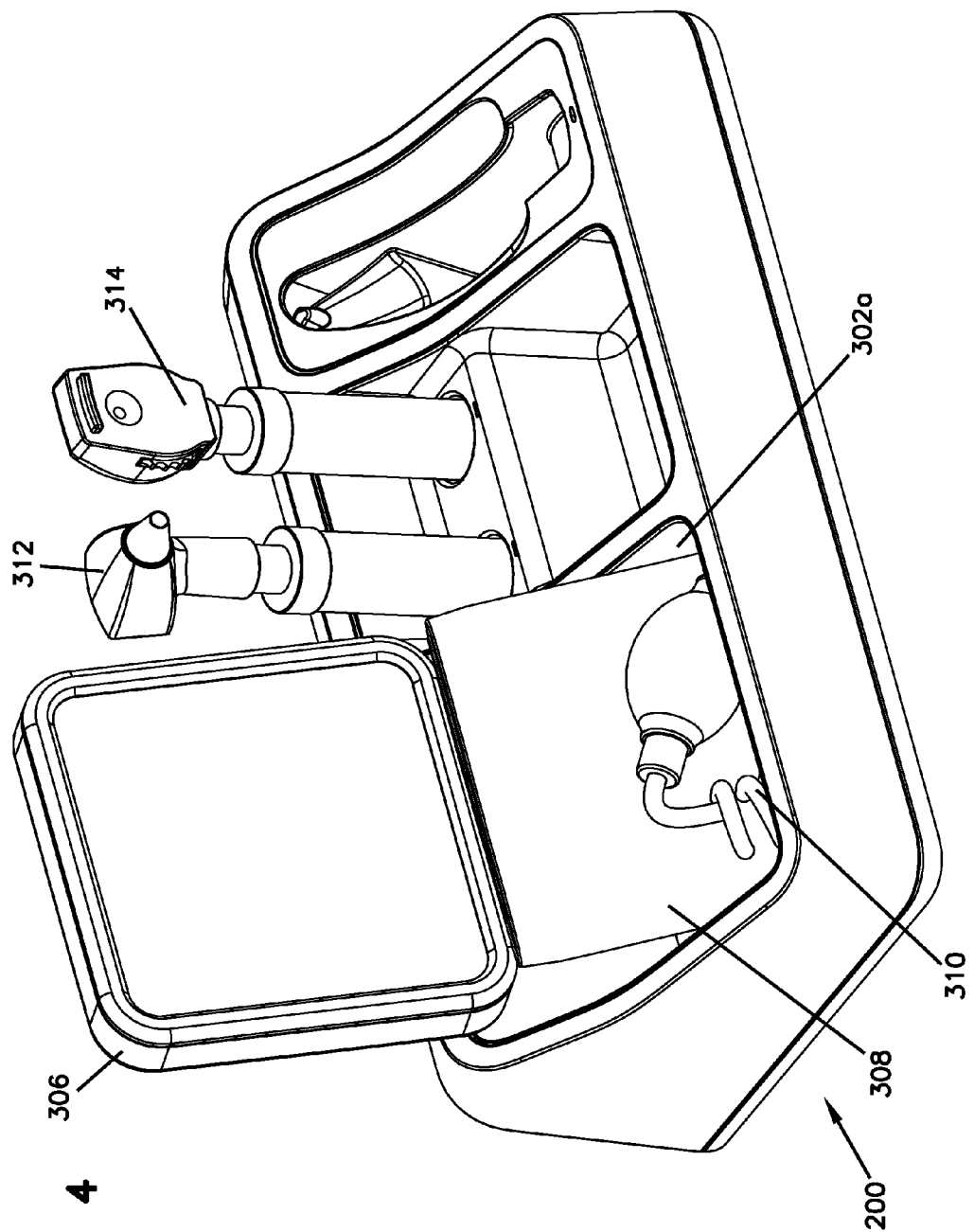
FIG. 4 shows the PMDS of FIG. 2 including medical instruments positioned thereto.
Figure 5:
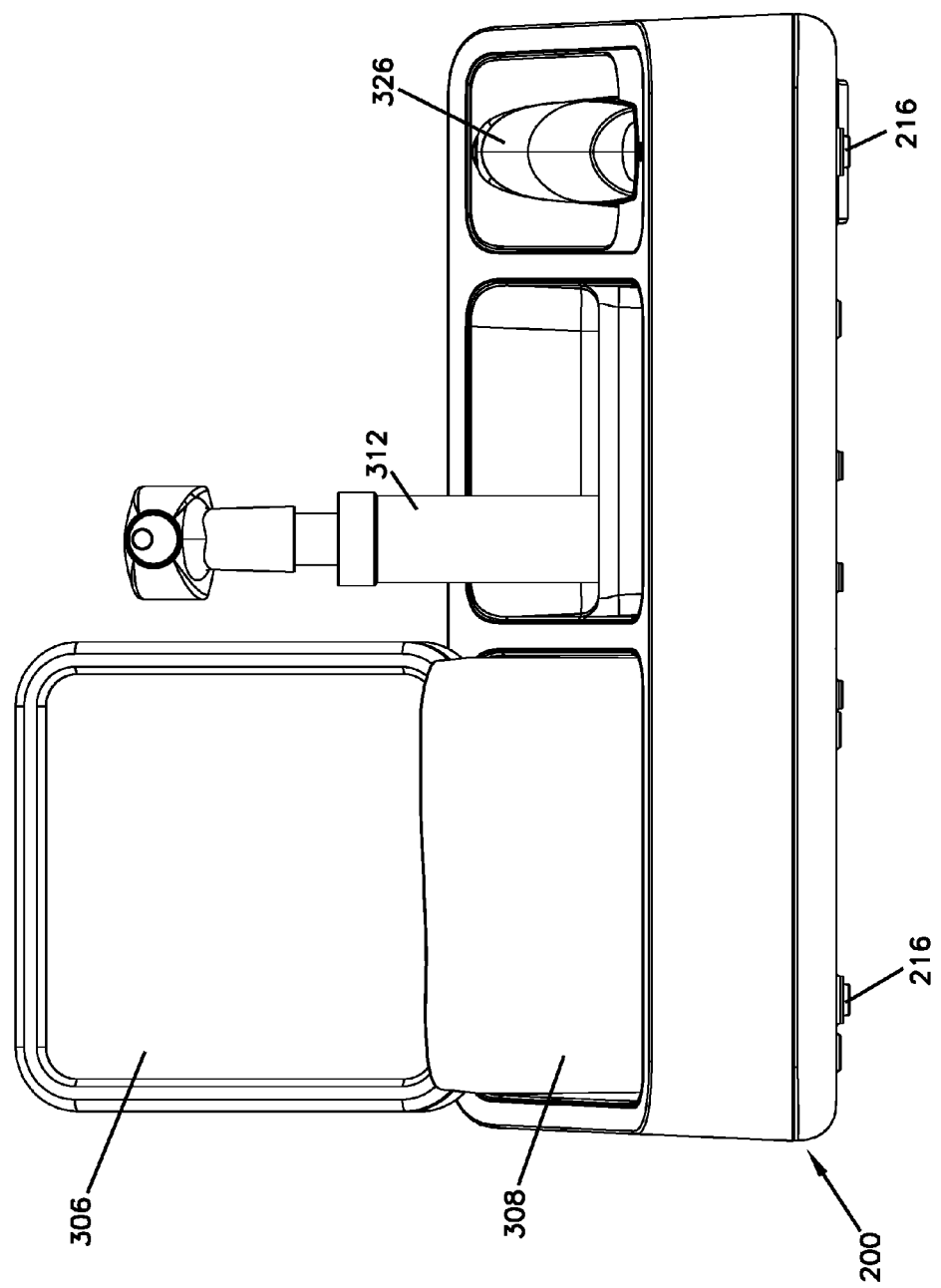
FIG. 5 shows a frontal view of the PMDS of FIG. 4.
Figure 6:
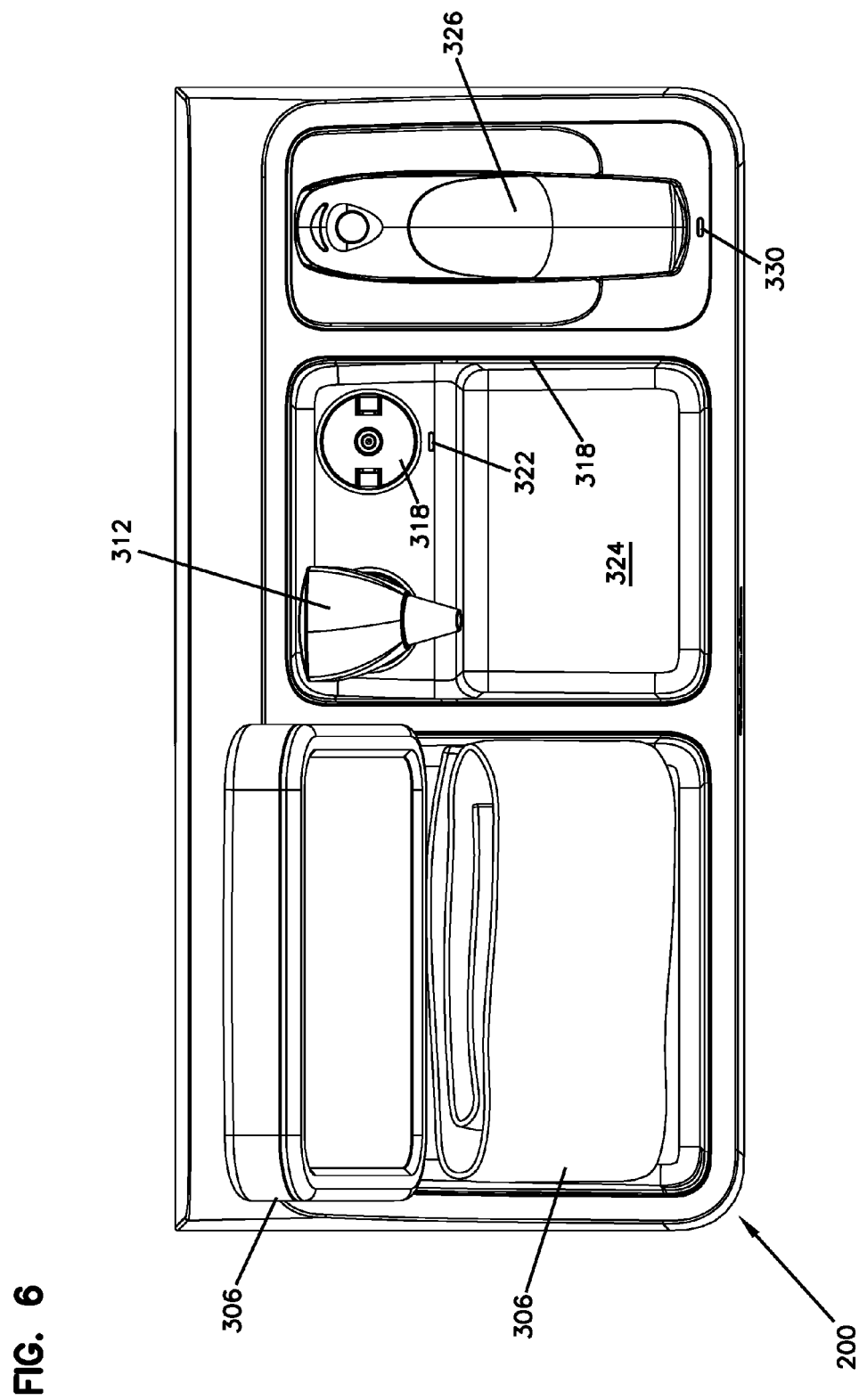
FIG. 6 shows a top view of the PMDS of FIG. 4.
Figure 7:
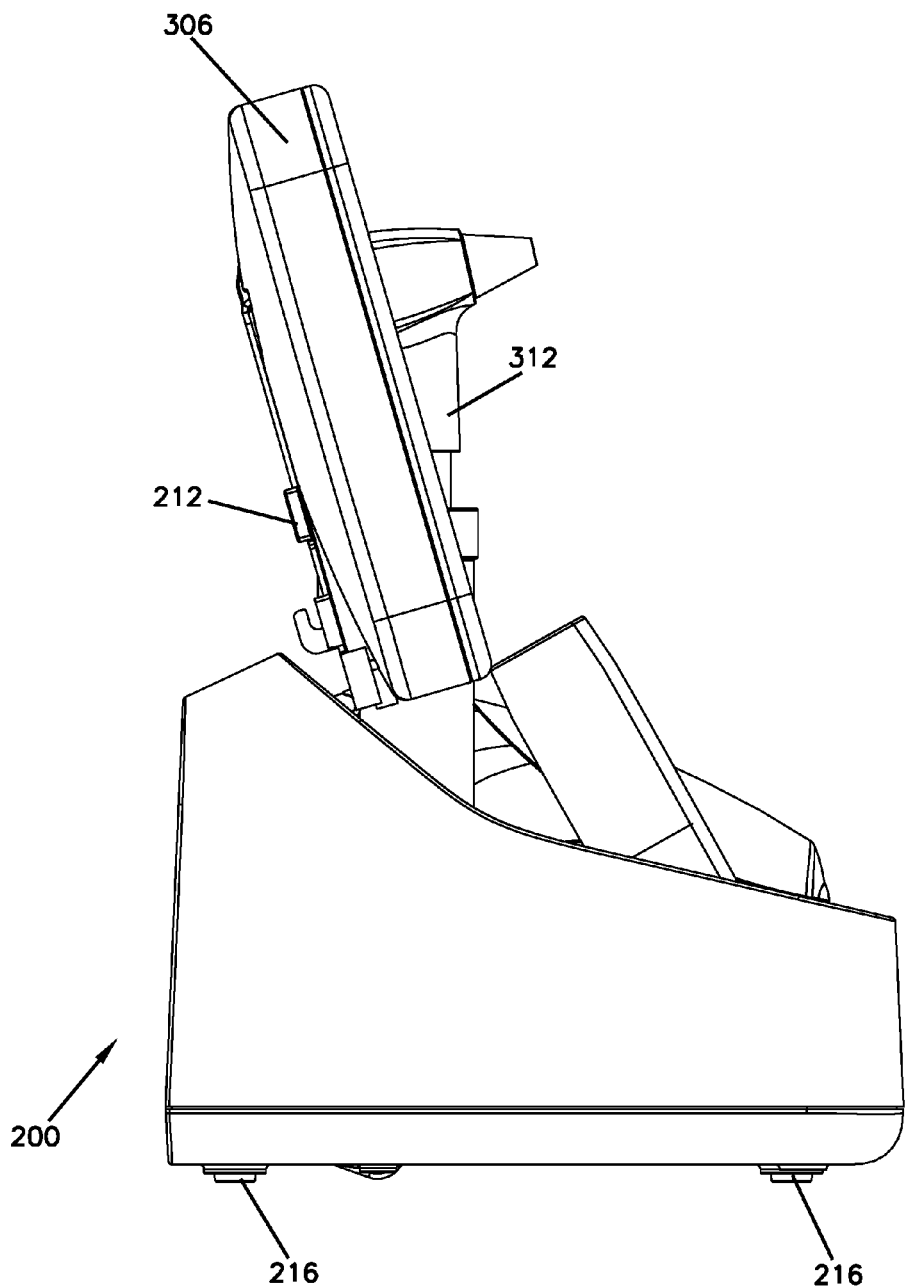
FIG. 7 shows a side view of the PMDS of FIG. 4.

For example, a first compartment 302a of the plurality of compartments 302 defines, or is generally arranged as, a receptacle for a blood pressure monitor 304 that includes an aneroid 306, a cuff 308, and a coiled tubing 310 (see, e.g., FIG. 3). An example blood pressure monitor includes the 767 aneroid with reusable cuff and coiled tubing from Welch Allyn, Inc. of Skaneateles Falls, N.Y. Other embodiments of the blood pressure monitor 304 are possible.

In example embodiments, the aneroid 306 is rigidly coupled to the bracket 212, which in turn is generally coupled to a portion of the first compartment 302a (see, e.g., FIG. 8). Both the cuff 308 and coiled tubing 310 can be stored within the first compartment 302a when not in use (see, e.g., FIG. 4). Other embodiments are possible.

A second compartment 302b of the plurality of compartments 302 defines, or is generally arranged as, a receptacle for an otoscope 312 and an ophthalmoscope 314 (see, e.g., FIG. 3). An example otoscope includes the Digital MacroView™ Otoscope from Welch Allyn, Inc. of Skaneateles Falls, N.Y. An example ophthalmoscope includes the Prestige™ Coaxial-Plus Ophthalmoscope also from Welch Allyn, Inc. Other embodiments of the otoscope 312 and ophthalmoscope 314 are possible.

The otoscope 312 and the ophthalmoscope 314 each may be positioned within either one of a first port 316 and a second port 318 (see, e.g., FIG. 3) of the second compartment 302b. In this example, the first port 316 and second port 318 are each generally configured or arranged to support either one of the otoscope and ophthalmoscope in an approximately vertical orientation. Additionally, the first port 316 and second port 318 are each coupled to the first power supply 210 shown in FIG. 2, which is generally positioned or arranged within the body 301.

When a positive connection is achieved between respective contacts 320 of a corresponding one of the first and second ports 316, 318 (see, e.g., FIG. 11) and compatible contacts (not shown) of the otoscope 312 and ophthalmoscope 314, an associated indicator 322 of the first port 316 and second port 318 is configured to specify whether either one of the otoscope 312 and ophthalmoscope 314 is receiving a charge, or is otherwise fully charged to capacity.

For example, in one embodiment, the indicator 322 of the first port 316 is a light emitting diode (LED) that is coupled to the first power supply 210. In this example, an illuminated LED may specify that either one of the otoscope 312 and ophthalmoscope 314 is receiving a charge from the first port 316; whereas a non-illuminated LED may specify that the otoscope 312 or ophthalmoscope 314 is fully charged to capacity. Other embodiments are possible.

In addition to the first port 316 and the second port 318, the second compartment 302b also includes a cavity 324 (see, e.g., FIG. 11). In general, the cavity 324 is configured or arranged to hold or otherwise support any type of appropriately sized item. For example, one or more reusable or otherwise disposable tips for one or both of the otoscope 312 and the ophthalmoscope 314 may be stored or placed within the cavity 324. Still other embodiments are possible.

A third compartment 302c of the plurality of compartments 302 defines, or is generally arranged as, a receptacle shaped as a cradle for a thermometer 326 (see, e.g., FIG. 3). An example thermometer includes the Braun ThermoScan® PRO 4000 Ear Thermometer from Welch Allyn, Inc. of Skaneateles Falls, N.Y. Other embodiments of the thermometer 326 are possible.

When positioned to the third compartment 302c, the thermometer 326 is supported in an approximately horizontal orientation (see, e.g., FIG. 8). Additionally, when a positive connection is achieved between respective contacts 328 (see, e.g., FIG. 11) that are coupled to the second power supply 211, which is generally positioned or arranged within the body 301, and compatible contacts (not shown) of the thermometer 326, an associated indicator 330 of the third compartment 302c is configured to specify whether the thermometer 326 is receiving a charge, or is otherwise fully charged to capacity, similar to the associated indicator 322 of the first port 316 and second port 318 described above.

In some embodiments, the third compartment 302c includes a removable tip holder 332 (see, e.g., FIG. 11) that permits a healthcare practitioner to selectively replace a tip (not shown) of the thermometer 326 on a patient-by-patient basis. Other embodiments are possible.

Referring now specifically to FIG. 9, a plurality of sockets 334 formed within the body 301 are coupled to an associated connection (not shown) on one or both of the first power supply 210 and second power supply 211 of FIG. 2. A power cord (not shown) can be connected to each one of the plurality of sockets 334 to enable the first power supply 210 and/or second power supply 211 to charge the otoscope 312, ophthalmoscope 314, and thermometer 326 when these respective instruments are positioned within a corresponding receptacle as described above. Other embodiments of the plurality of sockets 334 are possible. For example, in some embodiments, one or more of plurality of sockets 334 is configured as a universal serial bus (USB) data connection which can be used to supply power to and/or download data from one or more of the otoscope 312, ophthalmoscope 314, and thermometer 326 to an external computing device. Still other embodiments are possible.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An integrated portable medical diagnostic system, comprising:
    a blood pressure monitor;
    an otoscope;
    an ophthalmoscope;
    a thermometer;
    an apparatus including a body defining a plurality of compartments, wherein a first compartment defines a first receptacle for the blood pressure monitor, a second compartment adjacent the first compartment defines a second receptacle for the otoscope and the ophthalmoscope, and a third compartment adjacent the second compartment defines a third receptacle for the thermometer;
    at least one power supply arranged within the body;
    a plurality of ports each coupled to the at least one power supply and configured to supply power to either one of the otoscope and ophthalmoscope and to support either one of the otoscope and ophthalmoscope in an approximately vertical orientation;
    a bracket coupled to a portion of the first compartment, the bracket configured to support an aneroid of the blood pressure monitor;
    a light emitting diode associated with each one of the plurality of ports and configured to indicate a charging state of either one of the otoscope and ophthalmoscope when positioned in a corresponding one of the plurality of ports;
    wherein the third receptacle comprises a cradle arranged to support the thermometer in an approximately horizontal orientation, and wherein the cradle comprises contacts coupled to the at least one power supply and configured to supply power to the thermometer, with a light emitting diode being associated with the contacts and configured to indicate a charging state of the thermometer when positioned in the cradle.

2. The system of claim 1, wherein the second receptacle comprises a pocket arranged as storage for disposable and reusable tips of the otoscope and ophthalmoscope.

3. The system of claim 1, wherein at least a portion of the body is formed of a thermoplastic elastomer.

* * * * *